(12) United States Patent
Bentien (10) Patent No.: US 9,194,785 B2
(45) Date of Patent: Nov. 24, 2015

(54) SENSOR SYSTEM FOR DETECTING AND SPECIFYING INDIVIDUAL PARTICLES IN A FLUID

(75) Inventor: Anders Bentien, Skodstrup (DK)

(73) Assignee: Grundfos Management a/s, Bjerringbro (DK)

( * ) Notice: Subject to any disclaimer, the term of this patent is extended or adjusted under 35 U.S.C. 154(b) by 331 days.

(21) Appl. No.: 13/132,629

(22) PCT Filed: Dec. 2, 2009

(86) PCT No.: PCT/EP2009/008565
§ 371 (c)(1),
(2), (4) Date: Jun. 3, 2011

(87) PCT Pub. No.: WO2010/063455
PCT Pub. Date: Jun. 10, 2010

(65) Prior Publication Data
US 2011/0249255 A1    Oct. 13, 2011

(30) Foreign Application Priority Data

Dec. 3, 2008  (EP) ..................... 08020927

(51) Int. Cl.
*G01N 21/00*    (2006.01)
*G01N 15/14*    (2006.01)

(52) U.S. Cl.
CPC ........ *G01N 15/1459* (2013.01); *G01N 15/1434* (2013.01)

(58) Field of Classification Search
CPC ..................... G01N 15/1459; G01N 15/1434

USPC .......... 356/435, 441, 432, 433, 436, 440, 442
See application file for complete search history.

(56) References Cited

U.S. PATENT DOCUMENTS 3,413,464 A     11/1968  Kamentsky
3,819,277 A *    6/1974  Berthelot et al. ............. 356/435
3,822,095 A *    7/1974  Hirschfeld ...................... 356/39

(Continued)

FOREIGN PATENT DOCUMENTS

DE         4438833 A1    5/1996
EP         0713086 A1    5/1996
WO      2006017811 A2    2/2006

OTHER PUBLICATIONS

Int'l Search Report issued Apr. 8, 2010 in Int'l Application No. PCT/EP2009/008565.

*Primary Examiner* — Michael A Lyons
*Assistant Examiner* — Shawn Decenzo
(74) *Attorney, Agent, or Firm* — Panitch Schwarze Belisario & Nadel LLP (57) ABSTRACT

A sensor system for capturing and specifying individual particles (16) in a fluid includes a measurement cell (14) through which the fluid can flow, a light source (2; 30) that is arranged on the measurement cell (14) and creates a light beam (4; 36) passing through the measurement cell (14), and an intensity sensor (26; 44) that is arranged on the measurement cell (14) opposite the light source (2; 30) such that it captures the light beam exiting the measurement cell (14) and is designed for separately capturing the intensity ($I_A$, $I_B$) of the light beam in at least two different wavelength regions ($\lambda_A$, $\lambda_B$).

18 Claims, 9 Drawing Sheets

(56) References Cited

U.S. PATENT DOCUMENTS

| | | | |
|---|---|---|---|
| 3,864,044 A * | 2/1975 | Lyshkow | 356/436 |
| 4,168,294 A * | 9/1979 | Calzi et al. | 422/82.09 |
| 4,302,206 A * | 11/1981 | Profeta et al. | 436/106 |
| 4,702,607 A * | 10/1987 | Kinameri | 356/432 |
| 5,082,771 A | 1/1992 | Detty | |
| 5,175,438 A * | 12/1992 | Ikeda | 250/574 |
| 5,518,894 A | 5/1996 | Berg | |
| 5,663,057 A | 9/1997 | Drocourt et al. | |
| 5,723,031 A * | 3/1998 | Durr et al. | 204/451 |
| 5,751,839 A | 5/1998 | Drocourt et al. | |
| 5,763,203 A | 6/1998 | Ugelstad et al. | |
| 5,811,251 A | 9/1998 | Hirose et al. | |
| 5,858,697 A | 1/1999 | Groner et al. | |
| 5,891,394 A | 4/1999 | Drocourt et al. | |
| 5,948,684 A * | 9/1999 | Weigl et al. | 436/52 |
| 5,972,641 A | 10/1999 | Øfjord et al. | |
| 7,372,039 B2 * | 5/2008 | Tokhtuev et al. | 250/373 |
| 7,468,796 B2 * | 12/2008 | Luther et al. | 356/411 |
| 7,700,360 B2 * | 4/2010 | Everhart et al. | 436/71 |
| 8,179,533 B2 * | 5/2012 | Alameh | 356/445 |
| 2004/0011975 A1 * | 1/2004 | Nicoli et al. | 250/574 |
| 2007/0047868 A1 | 3/2007 | Beaulieu et al. | |

\* cited by examiner

SENSOR SYSTEM FOR DETECTING AND SPECIFYING INDIVIDUAL PARTICLES IN A FLUID

CROSS-REFERENCE TO RELATED APPLICATIONS

This application is a Section 371 of International Application No. PCT/EP2009/008565, filed Dec. 2, 2009, which was published in the German language on Jun. 10, 2010, under International Publication No. WO 2010/063455 A1 and the disclosure of which is incorporated herein by reference.

BACKGROUND OF THE INVENTION

Embodiments of the invention relate to a sensor system for detecting and specifying individual particles in a fluid.

In many applications, it is desirable to be able to detect microorganisms in an inexpensive and rapid manner, for example in the field of water supply. A widespread method is to let microorganisms grow on a culture medium for their detection. This as a rule lasts for 24 to 48 hours, so that the detection lasts quite some time. It is particularly with respect to a water supply, for example in the foodstuffs industry, that it is desirable to be able to detect bacteria as soon as possible, in order to be able to stop the production, as the case may be.

In the last years other methods have been developed, in order to be able to ascertain and quantify bacteria, which function in a quicker manner. Thereby however, the problem arises that the very simple functioning methods often require a very large number of bacteria, whilst methods which may detect a very low number of bacteria are very expensive.

U.S. Pat. No. 5,811,251 discloses a system, with which the number of living microorganisms is counted based on a CCD system. U.S. Pat. No. 5,972,641 and U.S. Pat. No. 5,518,894 disclose quick-test systems based on statistical methods, in order to determine the number of bacteria present. These methods also require up to eleven hours in order to ascertain a low number of bacteria.

Moreover, methods for detecting microorganisms based on fluorescence and laser light are known, for example, from U.S. Pat. No. 5,891,394, U.S. Pat. No. 5,858,697, U.S. Pat. No. 5,763,203, U.S. Pat. No. 5,751,839 and U.S. Pat. No. 5,663,057. The disadvantage of these methods is that an expensive laser light source is required. Moreover, immune tests are also known, which are used for detecting certain types of microorganisms. However, the application of these tests is limited and it is necessary to manufacture antibodies for each microorganism to be detected, which is time consuming and costly.

It is therefore desirable to provide an inexpensive sensor system for detecting and specifying individual particles in a fluid.

BRIEF SUMMARY OF THE INVENTION

The sensor system according to embodiments of the invention is based on the recognition of the different light absorption of particles which are located in a fluid. The sensor system includes a measurement cell through which fluid to be examined may flow. A light source is arranged on the measurement cell such that the light beam which is produced by the light source enters through the measurement cell. That is, a light beam running through the measurement cell is produced by the light source. Moreover, an intensity sensor is provided. This is arranged on the measurement cell lying opposite to the light source. This means the intensity sensor detects the light beam which is emitted by the light source and which runs through the measurement cell.

The measurement cell is preferably designed for the continuous passage of fluid therethrough. Thus the measurement cell may, for example, be integrated directly in a delivery conduit for water, for example drinking water, or into a pump system for example for water, so that the delivered fluid, preferably the complete delivered fluid, continuously flows through the measurement cell. Thereby, a continuous analysis of the fluid flowing through may be carried out, so that, for example, a continuous monitoring of the fluid or of the water is possible in a drinking water supply.

The intensity sensor is moreover designed for the separate detection of the intensity of the light beam in at least two different wavelength regions, which are detected by the light which is radiated from the light source.

This permits intensity changes, and in particular the light absorption of particles which pass through the light beam in the measurement cell, to be detected in at least two different wavelength regions. In this manner, it is possible to recognize characteristics of individual particles on account of their absorption rate at different wavelengths. In particular, it is possible to differentiate organic molecules from inorganic contamination in the fluid. Thus, the absorption rate of microorganisms in certain wavelength regions has a minimum and in further certain wavelength regions has a maximum. These characteristics permit a recognition. It is possible to accordingly recognize and specify individual microorganisms by way of detecting these wavelength regions with the help of the intensity sensor. In particular, the absorption spectrum of DNA and proteins of a microorganism are unique with regard to the local minimum and the local maximum in the absorption spectrum, so that a differentiation of inorganic contamination and other particles is possible.

If therefore, with regard to the sensor system according to embodiments of the invention, characteristic maxima or minima which are given to an evaluation system are detected by the intensity sensor in the two different wavelength regions, the sensor system may thus deduce the presence of microorganisms in the fluid flowing through the measurement cell. This detection may thus be effected with a very high accuracy. Individual microorganisms or bacteria may be detected in the fluid when it passes the light beam in the measurement cell. For detecting microorganisms or bacteria, the intensity sensor is designed in a suitably sensitive manner, in order to be able to detect such small particles, preferably smaller than 10 µm, further preferably smaller than 5 µm, in the form of individual particles.

According to embodiments of the invention, the characteristic absorption spectrum is to be used for recognizing bacteria or microorganisms. Only the absorption is to be determined with the help of the intensity sensor, but this under certain circumstances is difficult, since it may occur that a part of the light is scattered when it hits a particle. This in particular may be the case when the particle size lies in the same magnitude or smaller than the wavelength of the light beam. This scatter is difficult to measure. For this, a sensor must be applied, which may detect light which is scattered in different directions. For this reason, instead of determining the absorption itself, an intensity change or destructive interference may also be simply detected by the intensity sensor. This intensity change includes the actual absorption and the scattered share of the light, i.e., when a particle passes through the light beam, the intensity changes by the magnitude of the scattered light and the magnitude of the absorbed light. If in the subsequent description, one speaks of the absorption being determined, then this is not only to be understood as the actual absorption, but also the destructive interference or the intensity change which apart from the absorption, also contains a scattered light share.

The specific absorption spectrum of DNA and proteins, compared to inorganic contamination, is unique in that it has a very large absorption below a wavelength of roughly 300 nm. Moreover, local minima and maxima have been ascertained in the absorption spectrum in the ultraviolet region. These characteristics may be used in order to, with the help of the intensity sensor, detect microorganisms, and in particular individual microorganisms or bacteria. Preferably therefore, the intensity sensor is designed in a manner such that it may detect a wavelength region of smaller than 300 nm.

Thus it is not necessary to detect the complete absorption spectrum. Rather, it is sufficient to detect at least two wavelength regions, of which preferably at least one is situated in the UV range of smaller than 300 nm.

Preferably, the intensity sensor is designed in a manner such that a first wavelength region, in which the intensity may be separately detected by the intensity sensor, is a wavelength region in which the particles to be ascertained or detected have a local minimum in the light absorption. This is preferably a wavelength between 220 and 260 nm. This is the region in which microbes usually have a local minimum in the light absorption.

Further preferably, the intensity sensor is designed in a manner such that a second wavelength region, in which the intensity may be detected separately, is a wavelength region in which the particles to be ascertained or to be detected have a local maximum in the light absorption. This is preferably a wavelength between 240 and 290 nm. Microorganisms usually have a local maximum in the absorption rate in this wavelength region.

The intensity sensor is preferably designed such that it may detect the intensity of the light beam exiting from the measurement cell, at least in the two previously mentioned wavelength regions. The light source is thereby designed accordingly, so that it emits light of the wavelengths to be evaluated. Then, in this wavelength region, it is possible by way of the intensity sensor, to detect the light absorption and for example to deduce the presence of microorganisms, and, as the case may be, microorganisms with a characteristic absorption rate, for example on falling short of or exceeding predefined limit values.

According to a further preferred embodiment, the intensity sensor is designed in manner such that a third wavelength region is present, in which the intensity of the light beam exiting from the measurement cell may be separately detected by the intensity sensor. This third wavelength region which is likewise encompassed by the light which is irradiated from the light source, is thereby preferably a wavelength region in which the particles to be detected essentially absorb no light. This is preferably a region of a wavelength between 300 and 1100 nm. DNA, proteins and other constituents of microorganisms or bacteria usually have no significant absorption above a wavelength of 300 nm.

In order to be able to detect local minima or maxima in the previously mentioned characteristic wavelength regions, it is preferably also possible for the intensity sensor to be designed in a manner such that it detects the intensity in a larger spectrum which includes the previously mentioned characteristic wavelength regions and permits an assignment of the detected intensity to a wavelength region.

The sensor system comprises an evaluation device which is connected to the intensity sensor and which is designed in a manner such that it recognizes the type of a particle passing the light beam, by way of the detected intensities in at least two mentioned wavelength regions. Thus the evaluation device may compare the intensities currently detected in the two wavelength regions, with predefined limit values and may deduce a certain particle on exceeding or falling short of the limit values. In particular, the previously mentioned two, or further preferably three, wavelength regions are always considered together, i.e. certain particles are recognized by way of their respective absorption rate in the mentioned wavelength regions. The detection in the individual wavelength regions is thereby effected at the same time, so that it is always the respective intensity which is detected in all wavelengths, in which characteristic absorption rates for certain particles are to be expected. The simultaneous detection permits the continuous examination of a fluid flowing through the measurement cell.

Preferably, the evaluation device is designed in a manner such that for determining the absorptivity for a detected wavelength region, it subtracts the currently detected intensity from a previously detected or stored basic intensity of the light beam without particles. One obtains the current absorption rate in the respective wavelength region in this manner. In the case that a scattering of the light also occurs on hitting a particle, in this manner it is not the actual absorption which is detected, but an intensity change which is composed of the absorption and scatter. This however has an evaluatable, characteristic share of the absorption, i.e., the intensity change also has characteristic features in individual wavelength regions, and these features permit the identification of a microorganism. Thus for example, the intensity change may be effected in a wavelength region of smaller than 300 nm and with a second wavelength of greater than 300 nm. The detected destructive interference for a microorganism should lie below 300 nm above a certain limit value, which indicates a significant absorption in this wavelength region. On the other hand, in the wavelength region above 300 nm, the detected destructive interference should lie below a fixed limit value, from which one may recognize that the detected particle is not too large for a microbe. Irrespective of this, further preferably, the ratio of the two detected destructive interference values below and above 300 nm wavelength should lie above a preferred limit value, for example larger than 3.

For determining or for the identification of a certain microorganism, the intensity values determined at the two different wavelength regions or the determined absorption values, may be compared to one another, for example in a manner such that by way of the evaluation device, one detects whether both values are equally large or one of the values is larger than the other. One may deduce the type of the detected particle and in particular one may recognize whether it is the case of an inorganic particle or an organic particle such as a microbe, from the ratio of these values to one another.

Preferably, the evaluation device is designed in a manner such that its puts the determined intensity changes or absorptivities for two different wavelength regions in a ratio to one another and compares this ratio to a stored ratio value for a certain particle to be recognized. If the characteristic wavelengths are examined, in which characteristic minima and maxima occur at the absorption rate, the ratio of the values to one another, with the microorganisms to be detected, lies within certain limit values. In particular, a differentiation of certain microorganism from one another may also be possible by way of different limit values. For example, the ratio for bacteria usually lies in the region of 0 to 1. If the ratio lies outside this value, then one may conclude that it is not the case of a bacteria and it must be the case of a different type of particle.

According to embodiments of the invention, it is also possible to conclude the size of a particle. For this, the evaluation device is preferably designed such that it determines the size of a particle on the basis of the detected intensity, preferably by way of a detected absorptivity being related to a basic intensity of the light beam without particles. A higher absorption is to be expected with a larger particle, than with a small particle. The detection becomes independent of the respective basic intensity due to the relation the basic intensity, so that the calibration of the system is simplified. One does not need to compare absolute values with one another, but always only the relative values, and the basic intensity has no influence on the quality of the evaluation result. Since the basic intensity is detected again and again in the course of operation, changes of the sensor system thus also do not essentially influence the measurement result or the evaluation result.

The sensor system is preferably designed in a manner such that the light beam is focussed behind the light source, so that its focus is situated in the inside of the measurement cell, wherein the light beam in its focus region preferably has a cross-sectional area which is smaller than 60 times the cross-sectional area of the particle to be detected. An adequate measuring accuracy of the system is ensured by way of the focussing Further preferably, the focussing is effected in a manner such that the light beam in its focus region has a cross-sectional area which is smaller than 500 $\mu m^2$, further preferably smaller than 100 $\mu m^2$ or 24 $\mu m^2$.

Moreover, it is preferable for the cross-sectional area of the light beam not to spread by more than 100%, and preferably not more than 50%, from its focus region to the intensity sensor.

A collimator and/or an aperture are arranged in the beam course of the light beam, preferably behind the light source and in front of the entry into the measurement cell and/or behind the measurement cell and in front of the intensity sensor. An ideal beam guidance may be achieved by way of these elements and the beam in the measurement cell may be bundled or focused such that the desired measurement accuracy is achieved for detecting individual particles.

The light source may be designed such that it emits a wavelength spectrum which covers all the wavelength regions which may be detected by the intensity sensor for the measurement. Thus the complete required wavelength spectrum may be emitted by one and the same light source. However, according to a special embodiment, one envisages the light source being composed or formed of several, preferably monochromatic individual light sources with different wavelengths. These may be LEDs for example. By way of this construction, one may succeed in special wavelengths which are necessary for the measurement, according to embodiments of the invention, in the individual wavelength regions of the intensity sensor being emitted in a targeted manner. The measurement result may be improved by way of the limitation to these special wavelength regions. The monochromatic individual light sources may be arranged such that the light which is emitted by them is led together via fibre-optics in a common beam path which then passes through the measurement cell as a light beam. Thus a simultaneous detection of the light absorption is possible in all wavelength regions when a particle passes through the light beam in the measurement cell, which is thus composed of several individual light beams.

Preferably, the intensity sensor is accordingly also formed of several individual intensity sensors and includes a beam splitter which breaks down the light beam exiting from the measurement cell into beams of different wavelengths, which in each case are led to one of the individual intensity sensors. In this manner, a simple simultaneous detection of the intensities in the different wavelength regions is possible. Preferably, all individual intensity sensors are constructed in an equal manner and the assignment of the wavelength spectrum is effected only by way of the beam splitter. An inexpensive construction of the sensor system may be achieved in this manner.

Alternatively, it is also possible to provide an intensity sensor which detects the intensity of the incident light over a larger wavelength spectrum and permits an assignment of the detected intensity to the individual wavelengths. This assignment may be achieved, for example, by way of light of different wavelengths being deflected via a beam splitter, such as e.g., a prism, onto different regions of the sensor surface.

Proceeding from the light source, the light beam to the measurement cell is preferably led through a fibre-optic. In particular, with the use of several individual light sources, the individual light beams may be led from these individual light sources via fibre optics to the measurement cell and from there may be led together into a common beam path.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Figure 1:
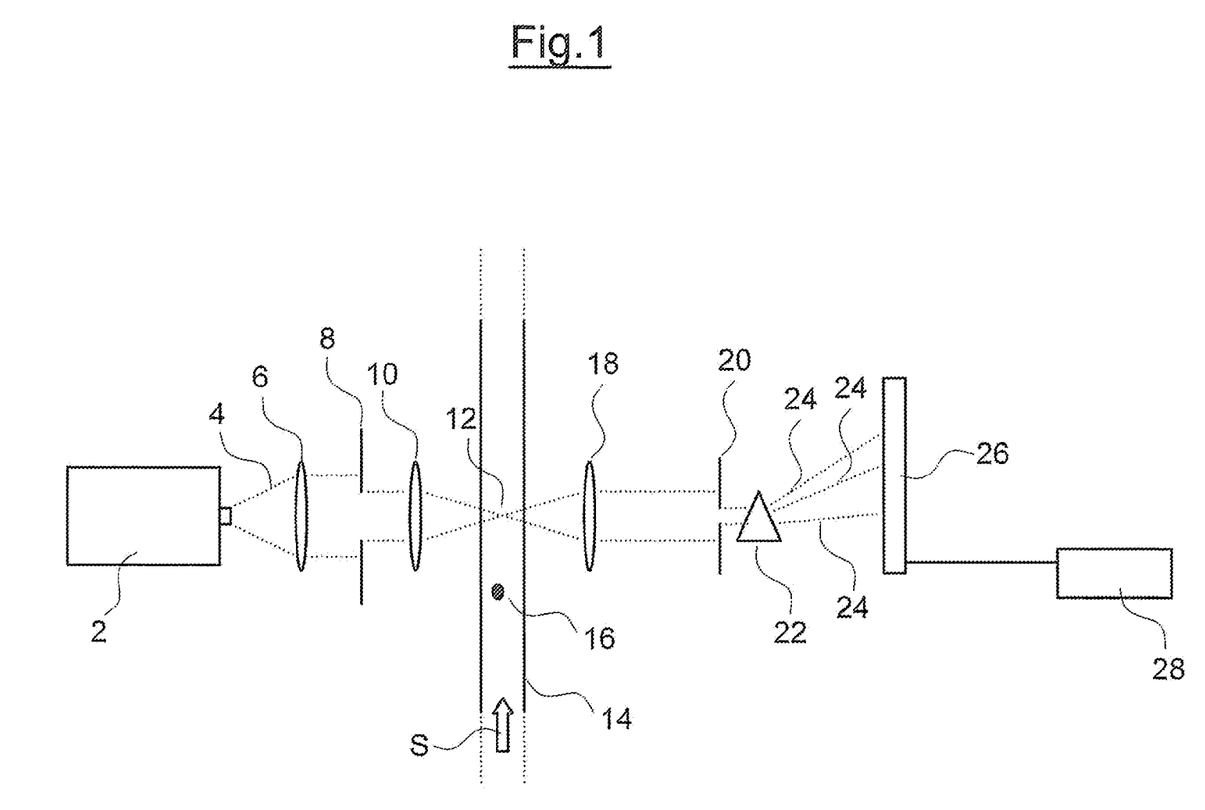
FIG. 1 schematically, a first embodiment according to the invention.

According to the first embodiment, which is shown in FIG. 1, a light source 2 is provided. This produces a light beam 4 with a band width of different wavelengths. Preferably, the light beam 4 covers a wavelength region of at least 20 nm to 1100 nm. The light beam 4, which exits from the light source 2, subsequently passes through a collimator lens 6 which produces a parallel bundled light beam and then subsequently runs through an aperture 8. The light beam which exits from the aperture 8 is bundled by way of a convergent lens 10 into a focus 12. The focus 12 is situated in the inside of a measurement cell 14, through which a fluid flows in the direction of the arrow S. The fluid in the measurement cell may contain individual particles 16 which flow with the fluid through the measurement cell 14. The walls of the measurement cell 14 at least in the entry and exit regions of the light beam 4, are designed in a transparent manner, so that the light beam proceeding from the convergent lens 10 may enter into the measurement cell 14 and exit at the oppositely lying side as is described hereinafter. Proceeding from the focus 12, the light beam 4 expands again and exits from the measurement cell 14 at the side which is opposite to the entry side. There, it again reaches a collimator lens 18 which again aligns the light beam in a parallel manner and subsequently runs through an aperture 20.

The light beam exiting from the aperture 20, hits a prism 22 which functions as a beam splitter or wavelength filter. The prism 22 deflects the light beam at different angles depending on its wavelength and thus splits the light beam into light beams 24 of different wavelengths. The light beams of different wavelengths thus hit the intensity sensor 26 in different regions. The intensity sensor 26 has a sensor surface which includes a multitude of measurement points or measurement regions and thus may determine the intensity of the incident light at different regions. That is, the intensity of the light of different wavelengths, which is incident on different regions on the sensor surface, may be detected individually by the intensity sensor 26. The intensity sensor 26 may thus detect the intensity of individual wavelength regions, since these wavelength regions are incident on different measurement points or measurement regions on the sensor surface.

If now a particle 16 passes through the light beam 4 which is focused in the focus 12 within the measurement cell 14, then an absorption of the light in the particle 16 occurs, by which means the intensity of the light exiting from the measurement cell 14 reduces. Thereby, the intensity in different wave regions reduces differently, which may be detected by the splitting of the wavelength regions in the prism 12 and the detection at different measurement regions of the intensity sensor 26. The absorption rate in certain wavelength regions is characteristic for the type of particle, so that the type of particle present may therefore be determined. For this, the intensity sensor 26 is connected to an evaluation device 28 which evaluates the preferably electrical signals which are produced by the intensity sensor 26 and represent the intensity.

Figure 2:
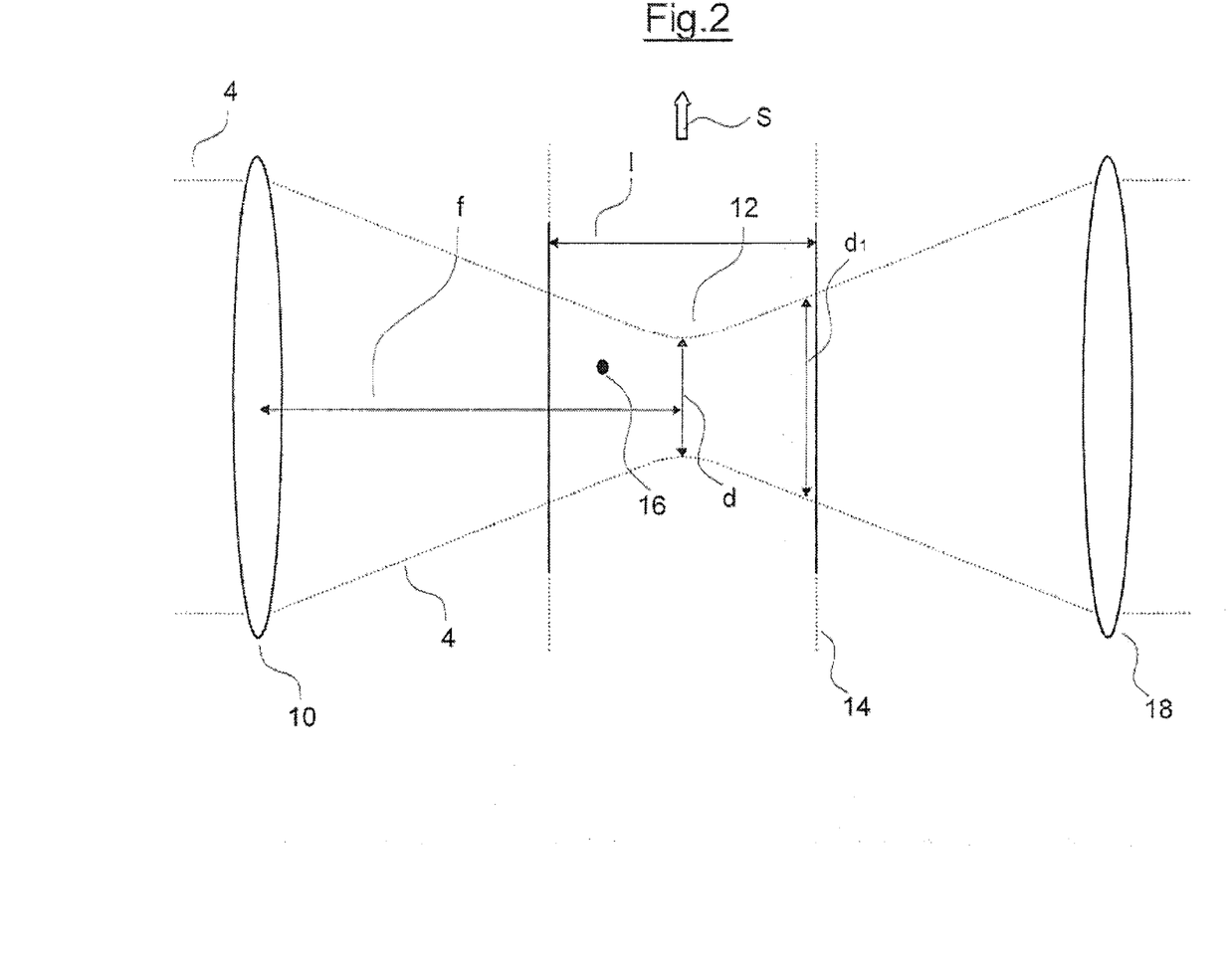
FIG. 2 a detailed view of the measurement cell and of the light beam running through this, according to FIG. 1, FIG. 3 schematically, a second embodiment of the invention, FIG. 4 schematically, an enlarged view of the measurement cell of the embodiment according to FIG. 3, FIG. 5 schematically, the absorption curves of DNA, protein and microbes, which are used for the recognition of particles such as microbes, FIG. 6 schematically, the absorption curves when a particle passes through the measurement cell, FIG. 7 schematically, the absorption curves when a particle which is not identified as a microbe, passes through the measurement cell, FIG. 8 schematically, the intensity course when a particle passes through the measurement cell, and FIG. 9 schematically, the intensity course when a participle which is not identified as a microbe, passes through the measurement cell.

FIG. 2 in detail shows how the light beam 4 is focused into the measurement cell 14. The convergent lens 10 has a focal width f and focuses the light beam 4 into the focus 12. The focus 12 thereby is situated in the middle of the measurement cell 14 in its width direction 1. In the passage direction of the light beam, the measurement cell 14 has a width 1. The diameter of the light beam 4 in the focus 12 has the diameter d. Proceeding from the focus 12, the light beam expands to the oppositely lying exit wall of the measurement cell 14 through which the light beam exits from the measurement cell 14, so that it has a diameter $d_1$ there. Subsequently, the light beam 4 is incident on the convergent lens 18. The particles 16 to be detected, as a rule, have a size of a few µm and are preferably microbes. In order to be able to detect individual microbes, it is important for the beam diameter d in the inside of the measurement cell 14 not to be too large. It must lie in the same magnitude range as the particles to be detected, since the absorption to be measured would otherwise be too high. The cross-sectional area in the focus 12 preferably lies in the region of a few µm². The diameter d in the focus preferably lies at roughly $1.22\lambda \times f/d_0$, wherein $d_0$ is the diameter of the light beam at the exit from the aperture 8 and $\lambda$ is the wavelength of the light. With a diameter $d_0$ between 1 mm and 2 mm and a focal width f of roughly 30 mm, with a measurement cell width 1 of roughly 200 mm and a wavelength of roughly 0.3 µm, one may achieve a beam diameter in the focal point of roughly 8 µm and at the exit of roughly 10 to 11 µm. By way of this, one may recognize that it is possible to focus the beam in an adequately small manner, in order to bring the beam diameter, with regard to the magnitude range, into the region of the size of the particles 16 to be detected, so that its absorption at the intensity sensor 26 is clearly measurable.

Figure 3:
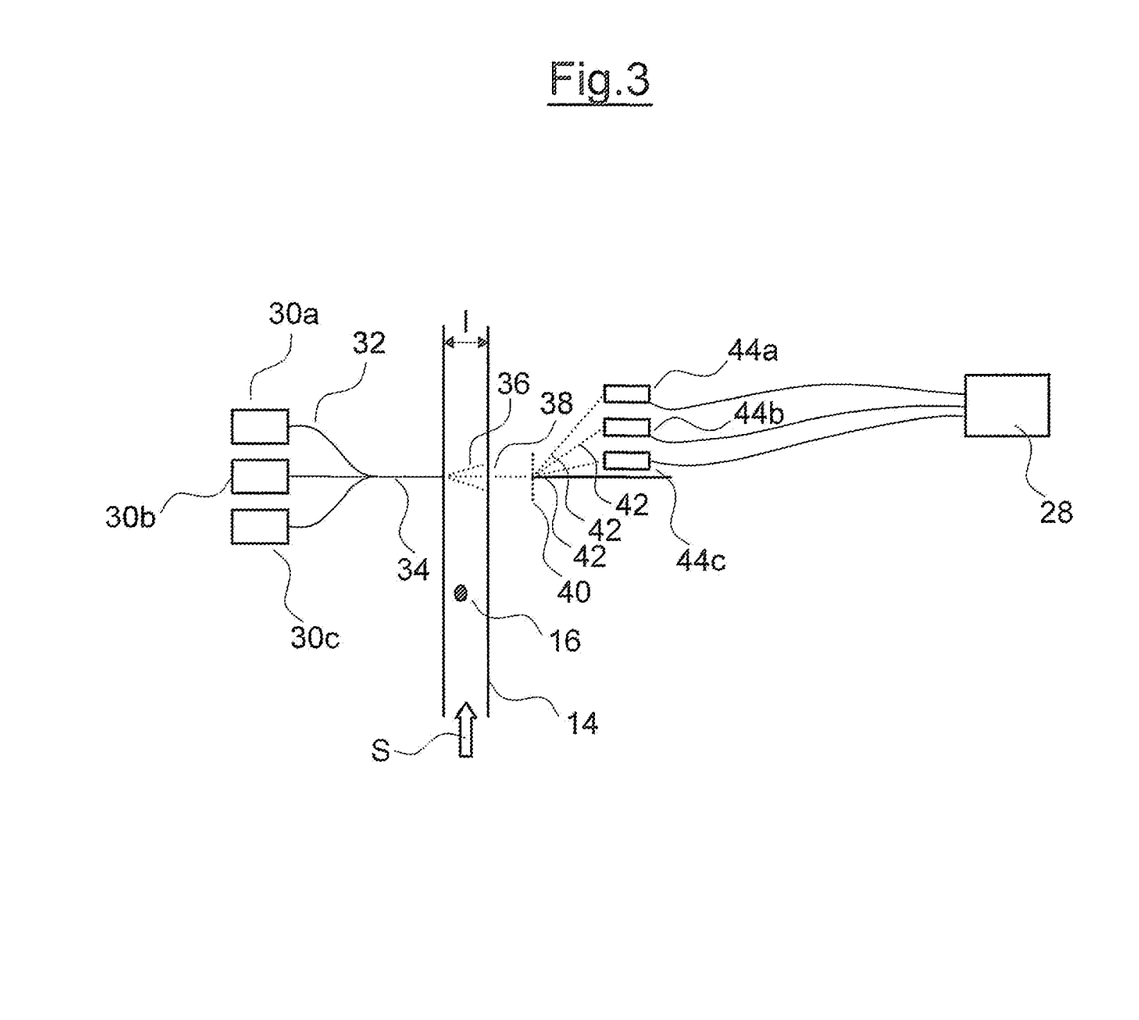

FIG. 3 shows a second possible embodiment of the invention, wherein with this second embodiment, the same components according to the preceding description are characterized with the same reference numerals. With this second embodiment, the light source is formed from three monochromatic individual light sources 30a, 30b and 30c. The light which exits from the individual light sources is led to the measurement cell 14 via three fibre optics 32. With the monochromatic individual light sources 30a, 30b and 30c, it may for example be the case of light diodes with different wavelengths. That is, the three monochromatic individual light sources emit light with different wavelengths. The wavelengths are selected such that they correspond to the characteristic regions which here are to be examined for differentiating the particles. The fibre-optics 32 run out into a common fibre-optic 34 which then leads the light to the measurement cell 14. On exit from the fibre optic 34, the light beam 36 expands slightly when it runs through the measurement cell 14 in its width direction 1. The light beam 36 exiting from the fibre-optic 34 however, on running through the measurement cell, expands only so slightly, that one may make do without a collimator here. A small opening or aperture 38, through which the light beam exits from the measurement cell 14, is formed lying opposite the exit from the fibre optic 34, in the measurement cell 14. Subsequently, the light beam passes through a beam splitter 40, for example in the form of a prism or diffraction grating which, as explained by way of FIG. 1, divides the light beam into individual light beams 42 of different wavelengths. The individual light beams 42 are diffracted or refracted to a different extent, so that they exit the beam splitter 40 at different angles and thus are led separately from one another to individual intensity sensor 44a, 44b and 44c. The individual intensity sensors 44a, 44b and 44c detect the light intensities at the different wavelengths, by way of the different wavelength regions being led to them individually. The intensity sensors 44, just as with the first embodiment example, are connected to an evaluation device 28 which carries out the evaluation of the detected intensities in a manner such that individual particles may be identified by way of the absorption rates at different wavelengths.

Figure 4:
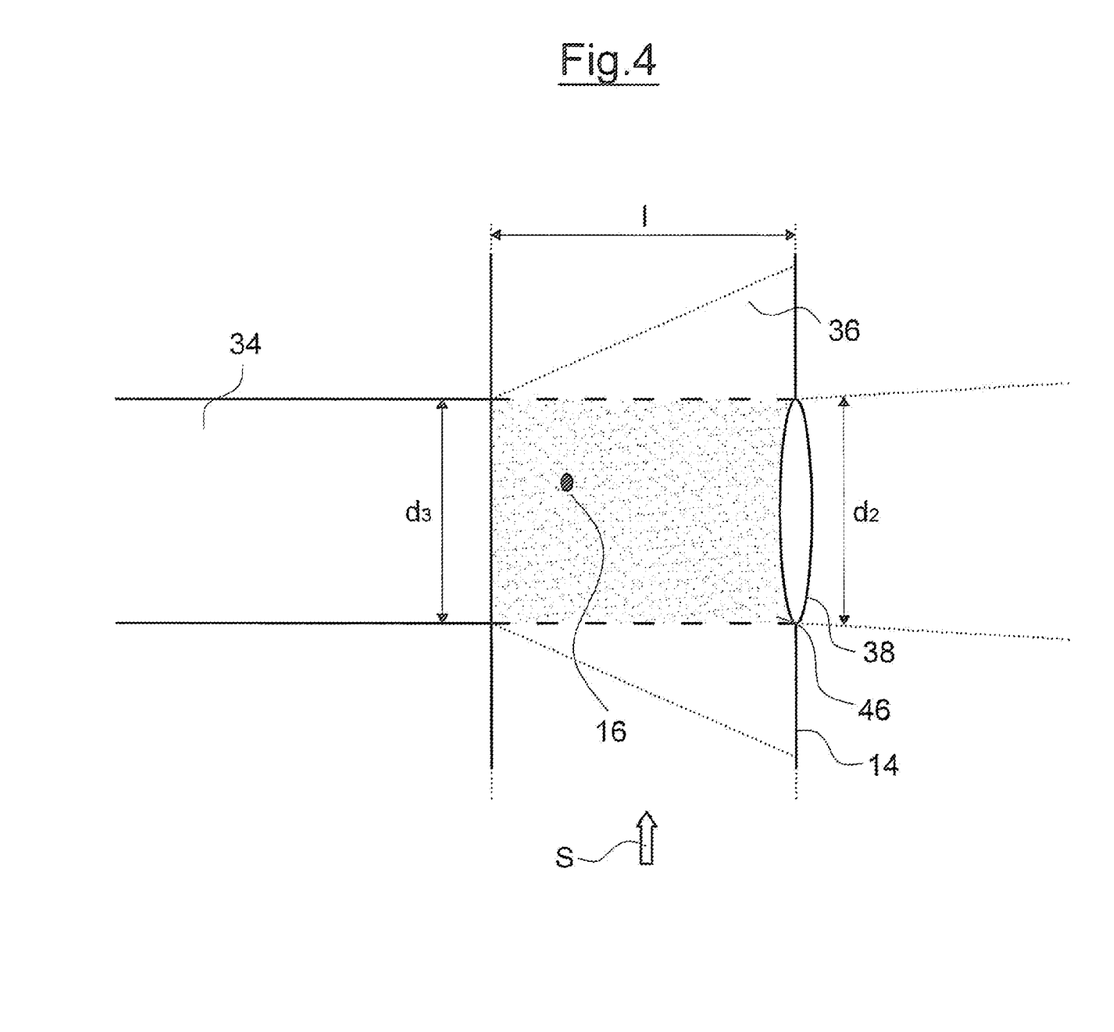

FIG. 4 in a detailed view shows the passage of the light beam 36 through the measurement cell 14. The fibre optic 34 ends at a wall of the measurement cell 14. There, the light beam 36 exits from the fibre optic 34 and runs through the measurement cell in its width direction 1 up to the oppositely lying wall. Thereby, the light beam expands. In order to achieve a defined measurement volume, an opening or aperture 38, through which the light beam exits from the measurement cell 14, is formed at the exit side of the measurement cell in the wall. Thus one succeeds in only the region 46 of the light beam 36 which is delimited by the dashed lines in FIG. 4, being used for the measurement or detection and the specification of particles 16. Thus a defined measurement volume is created in the inside of the measurement cell 14. With this embodiment too, the width 1 of the measurement cell preferably lies in the region of 200 µm to 1000 µm. The diameter of the region 46, i.e. of the measurement volume, the diameter $d_2$ of the beam exiting from the aperture 38 as well as the diameter $d_3$ of the fibre optic 34 preferably lie in the region of 5 μm to 20 μm, i.e. in a similar magnitude to that of the particles 16 to be detected, so that detectable intensity changes at the sensors 44 occur with the passage of the particles 16 through the region 46.

It is to be understood that with the second embodiment, instead of the individual intensity sensors 44, one may also apply an intensity sensor 26 as has been described by way of FIG. 1. Alternatively, also with the first embodiment, one may apply an intensity sensor consisting of several individual intensity sensors.

Figure 5:
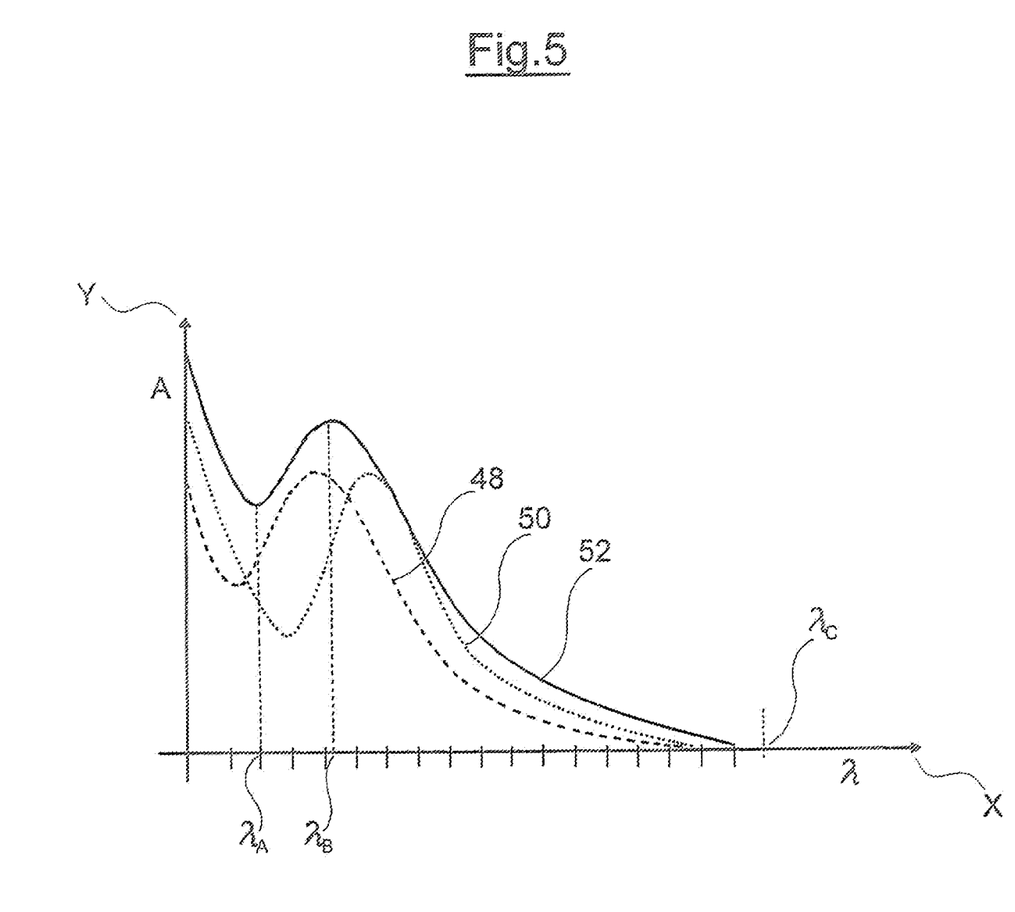

The characteristic absorption of DNA, protein and microbes is explained by way of FIG. 5. In the diagram in FIG. 5, the wavelength is plotted on the X-axis and the detected absorption A on the Y-axis. Three curves 48, 50, and 52 are drawn in the diagram. The absorption curve 48 is the absorption curve of DNA, the absorption curve 50 of protein and the absorption curve 52 is the absorption curve of a microbe. Three specific wavelengths $\lambda_A$, $\lambda_B$ and $\lambda_C$ are observed for determination and specification of the particles 16. Thereby, one may recognize that with the wavelength $\lambda_A$, the absorption curve 52 of the microbe has a local minimum. With the wavelength $\lambda_B$, the absorption curve 52 has a local maximum and with the wavelength $\lambda_C$ one may essentially ascertain no absorption. This distribution of the local maxima and minima of the absorption at different wavelengths is unique for microbes, so that individual particles may be detected by the sensor system and may be specified as microbes or bacteria by way of local minima and maxima at the mentioned wavelengths $\lambda_A$, $\lambda_B$ and $\lambda_C$ being evaluated. For this, the light source according to FIG. 1 preferably produces a wavelength spectrum which includes the wavelengths $\lambda_A$, $\lambda_B$ and $\lambda_C$. With the second embodiment, accordingly three monochromatic light sources 30a, 30b and 30c are used, of which one emits light with the wavelength $\lambda_A$, one light with the wavelength $\lambda_B$ and one light with the wavelength $\lambda_C$. Accordingly, three intensity sensors 44a, 44b and 44c are used, in order to evaluate the intensities at the three different wavelengths. The wavelengths $\lambda_A$, $\lambda_B$ and $\lambda_C$ are separated from one another in the light beams 42 which are deflected at different angles, so that in each case one of the mentioned wavelengths is incident on one of the individual intensity sensors 44a, 44b and 44c. The wavelength $\lambda_A$ preferably lies in the region between 220 and 260 nm, the wavelength $\lambda_B$ preferably lies in the region between 240 and 290 nm and the wavelength $\lambda_C$ in the region between 300 and 1100 nm.

Figure 6:
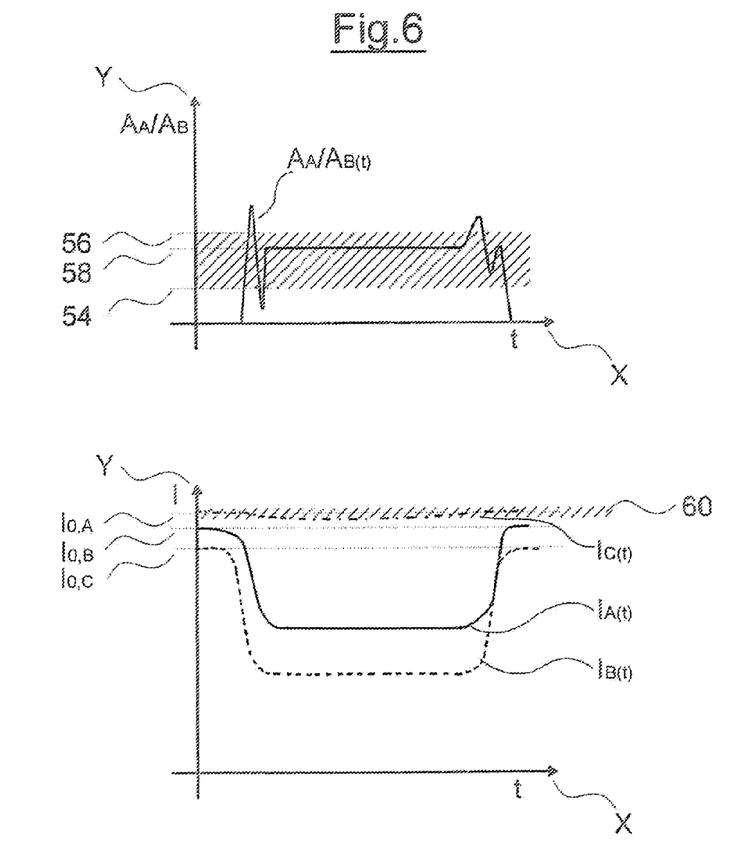
Figure 7:
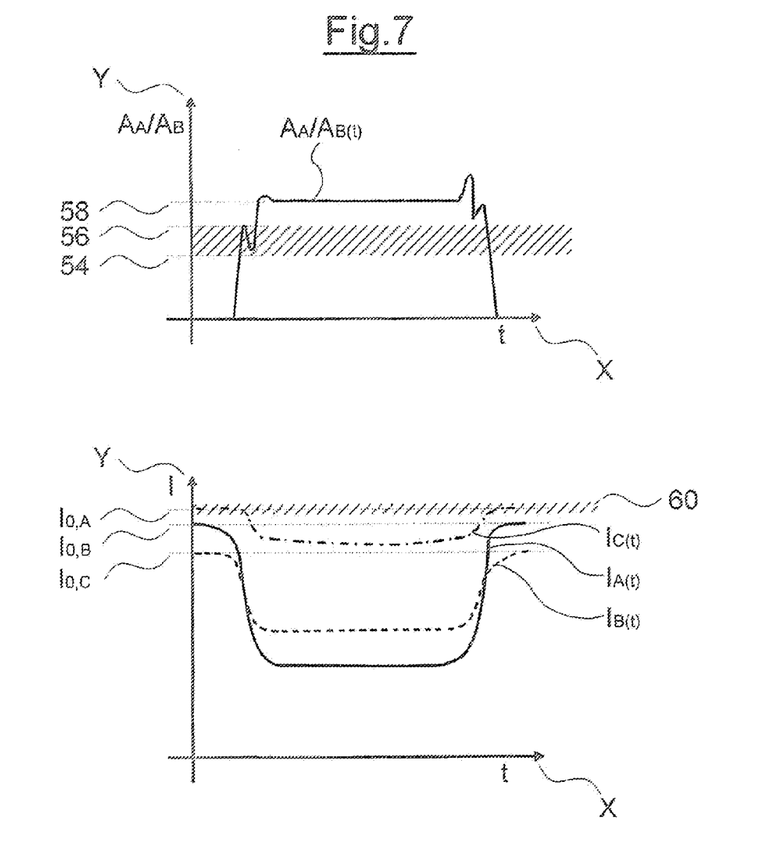

Once again, the difference of a microbe and another type of particle on account of the evaluation of the absorption at different wavelengths is explained in more detail by way of FIGS. 6 and 7. FIG. 6 shows two diagrams above one another. The course of time t is plotted on the X-axis. In the lower diagram, the intensity 1 as is detected by the intensity sensor 26 or the intensity sensors 24, is plotted on the Y-axis. The three horizontal curves $I_{0,A}$, $I_{0,B}$ and $I_{0,C}$ are the background intensities or base intensities at the three different wavelengths $\lambda_A$, $\lambda_B$ and $\lambda_C$ (see FIG. 5), as are measured by the intensity sensors 26 or 44 when no particles 16 flow through the measurement cell 14. The three temporal intensity courses $I_{0,A}(t)$, $I_{0,B}(t)$ and $I_{0,C}(t)$ show the temporal intensity courses which are measured at the wavelengths $\lambda_A$, $\lambda_B$ and $\lambda_C$ when particles pass through the light beam in the measurement cell 14. The absorption rates $A_A(t)$, $A_B(t)$ and $A_C(t)$ when particles pass through the beam path in the measurement cell 14, are determined on the basis of these detected intensities. These absorptions are determined according to the following equations: $A_A(t)=I_{0,A}-I_A(t)$, $A_B(t)=I_{0,B}-I_B(t)$ and $A_C(t)=I_{0,C}-I_C(t)$.

In the upper diagram in FIG. 6, the time-dependent ratio of the absorption rates $A_A$ to $A_B$, (i.e., $A_A/A_B(t)$) is plotted over time. That is, the ratio of the absorption rates $A_A/A_B$ are plotted on the Y-axis. One may determine by way of this ratio whether the particle 16 is a microbe. If the particle 16 is situated completely in the beam, the ratio $A_A/A_B$ has a constant value 58 between the limit values 54 and 56. The limit values 54 and 56 preferably lie at 0.2 and 1. In order to determine whether it is indeed the case of a microbe, furthermore the intensity curve $I_C(t)$ at the wavelength $\lambda_C$ is also taken into account. The intensity $I_C(t)$ lies above the complete temporal course in the hatched region 60, thus does not essentially reduce when a particle 16 passes through the light beam. As explained above, it is characteristic of microbes that they have essentially no absorption above a certain wavelength region. Inasmuch as this is concerned, by way of this and together with the ratio $A_A/A_B$ between the limit values 54 and 56, one may recognize that the particle 16 which has passed the light beam, is the case of a microbe.

FIG. 7 now shows diagrams according to those of FIG. 6 for the case that a particle 16 other than a microbe passes through the light beam. In this case too, the absorption ratio $A_A/A_B(t)$ has a constant value 58 when the particle 16 is located completely in the light beam in the measurement cell 14. However, this constant value 58 lies outside the limit values 54 and 56, i.e., here there are not the expected maxima and minima at the wavelengths $\lambda_A$ and $\lambda_B$, as is characteristic for microbes, which has been explained by way of FIG. 5. This leads to the larger absorption ratio $A_A/A_B$ with the value 58. Moreover, here too, the intensity $I_C(t)$ lies outside the region 60, from which one may recognize that the particle is not a microbe, since microbes have essentially no absorption at the wavelength region $\lambda_C$, so that here a reduction of the intensity would not occur.

The differentiation of a microbe from a different type of particle on the basis of the absorption rate has been explained by way of FIGS. 6 and 7. As described above, the absorption rate may not always be determined alone from the detected intensity change, since a scatter of the light might yet occur. In a corresponding manner, the recognition of a microbe may however be recognized also alone by way of the intensity change (i.e., by way of the effected destructive interference), which includes the absorption and scatter. A differentiation is also only possible by way of two different wavelengths. This is described by way of example with regard to FIGS. 8 and 9. In the lower part of the diagrams according to FIGS. 8 and 9, the intensity 1 is plotted over time t, as also in t FIGS. 6 and 7.

Figure 8:
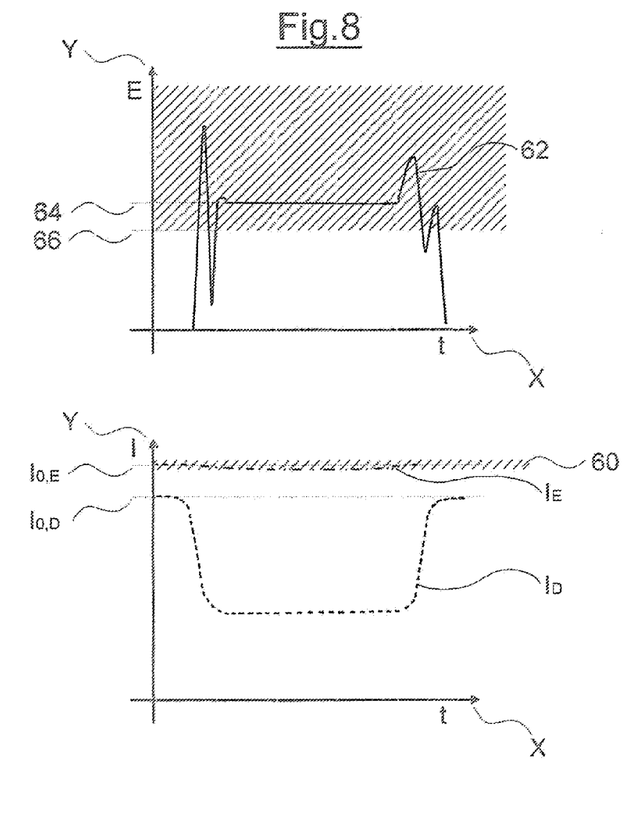

Two intensity courses $I_D$ and $I_E$ are plotted over time t in the lower diagram of FIG. 8. Thereby, the intensities $I_E$ and $I_D$ correspond to intensities at two different wavelengths $\lambda_E$ and $\lambda_D$. The wavelength $\lambda_D$ preferably lies below 300 nm and the wavelength $\lambda_E$ preferably above 300 nm. The intensity courses $I_{0,E}$ and $I_{0,D}$ which are represented as straight lines in FIG. 8, represent the intensity courses at the mentioned wavelengths when no particle passes through the light beam. The intensity courses $I_E$ and $I_D$ result when a microbe passes through the light beam. One may recognise that with the wavelength $\lambda_D$, the intensity $I_D$ decreases significantly (i.e., in this wavelength region, a high destructive interference occurs on the passage of a microbe). In the second wavelength region $\lambda_E$ however, only a small intensity change occurs, which lies within a limit value region 60. A microbe may be recognized in this way. In the upper diagram in FIG. 8, the destructive interference E is plotted over time t. The destructive interferences at the two different wavelengths $\lambda_E$ and $\lambda_D$ result as $E_D=I_{0,D}-I_D$ and $E_E=I_{0,E}-I_E$. The upper curve in FIG.

8 represents the ratio $E_D/E_E(t)$. This is curve 62. If the particle has completely entered into the light beam, this value 62 lies on the straight line 64 above a limit value 66. This is 3 for example. This ratio above a limit value 66 likewise indicates that it is the case of a microbe.

Figure 9:
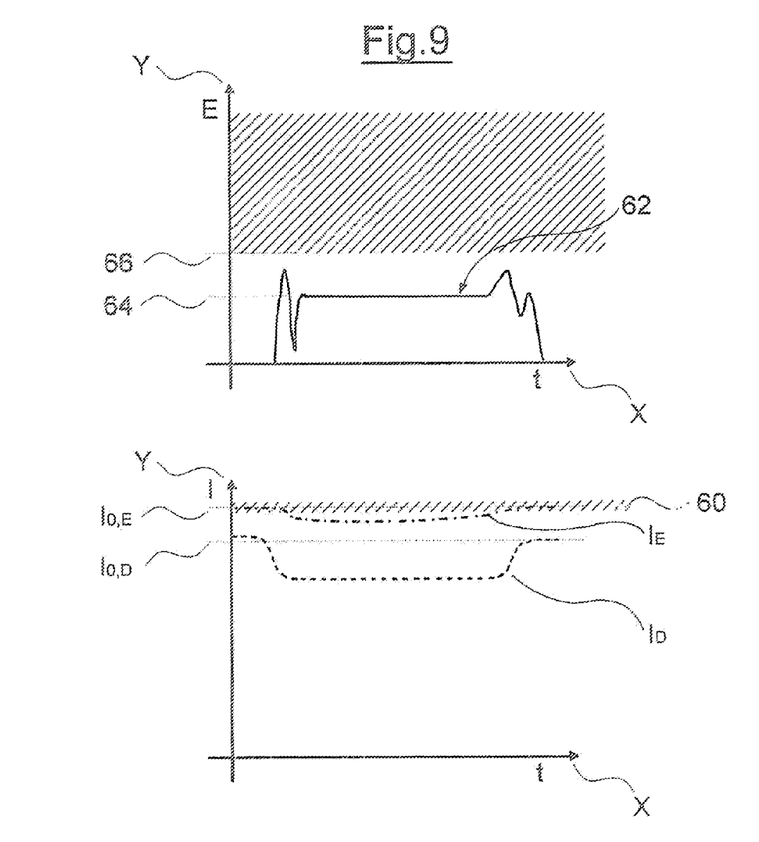

FIG. 9 now shows diagrams corresponding to those of FIG. 8, for the case that the particle, which passes through the light beam, is not a microbe. One may recognize that the intensity change of the intensity course $I_D$ is significantly smaller than in the case that a microbe passes through the light beam. Simultaneously, the intensity $I_E$ reduces to a greater extent, so that the curve leaves the limit value region 60. Here too, the destructive interferences $E_E$ and $E_D$ are formed in the manner described above and set into a ratio, which is represented as a curve 62 in the upper diagram. Here, one may recognize that the region, which runs as a straight line and indicates the passage of the particle through the light beam, is situated at the constant value 64', which lies below the limit value 66. This indicates that here, it is not a microbe which passes through the light beam, but a different type of particle.

This evaluation described by way of FIGS. 5 to 9, is carried out in the sensor system by the evaluation device 28 by way of the exits signals of the intensity sensors 28 or 44.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A sensor system for detecting and specifying individual microorganisms in a fluid, comprising:
   a measurement cell integrated into a delivery conduit for the fluid that delivers a continuous flow of the fluid, the fluid flowing through the measurement cell,
   a light source which is arranged on the measurement cell and produces a light beam running through the measurement cell, the light beam in its focus region having a cross-sectional area which is smaller than sixty times a cross-sectional area of the microorganism to be detected,
   an intensity sensor which is arranged on the measurement cell and lying opposite the light source to detect the light beam exiting from the measurement cell and is designed for the separate detection of an intensity of the light beam in at least two different wavelength regions, and
   an evaluation device which is connected to the intensity sensor and which is configured to recognize the type of a microorganism passing through the light beam by way of the detected intensities in the two wavelength regions, wherein the evaluation device is configured to:
   for determining the absorptivity of a detected wavelength region, subtract the currently detected intensity from a previously detected or stored base intensity of the light beam without particles,
   calculate a ratio of the two absorptivities for the two different wavelengths, and
   detect a microorganism if the calculated ratio is above a first limit value and only one of the two absorptivities is above a respective second limit value.

2. The sensor system according to claim 1, wherein the intensity sensor is designed in a manner such that a first wavelength region, in which the intensity may be detected separately, is a wavelength region of smaller than 300 nm.

3. The sensor system according to claim 1, wherein the intensity sensor is designed in a manner such that a first wavelength region, in which the intensity may be detected separately, is a wavelength region, in which the microorganisms to be detected have a local minimum in light absorption.

4. The sensor system according to claim 3, wherein the first wavelength region lies between 220 and 260 nm.

5. The sensor system according to claim 1, wherein the intensity sensor is designed in a manner such that a second wavelength region, in which the intensity may be detected separately, is a wavelength region in which the microorganisms to be detected have a local maximum in light absorption.

6. The sensor system according to claim 5, wherein the second wavelength region lies between 240 and 290 nm.

7. The sensor system according to claim 1, wherein the intensity sensor is designed in a manner such that a third wavelength region, in which the intensity may be detected separately, is a wavelength region in which the microorganisms to be detected essentially absorb no light.

8. The sensor system according to claim 7, wherein the third wavelength region lies between 300 and 1100 nm.

9. The sensor system according to claim 1, wherein the evaluation device is configured to determine the size of a microorganism on the basis of the detected intensity.

10. The sensor system according to claim 9, wherein the evaluation device determines the size of the microorganism by comparing the detected absorptivity to a base intensity of the light beam without particles.

11. The sensor system according to claim 1, wherein the light beam is focused behind the light source in a manner such that a focus is situated in the inside of the measurement cell, wherein the light beam in its focus region has a cross-sectional area which is smaller than 60-times a cross-sectional area of the microorganisms to be detected.

12. The sensor system according to claim 11, wherein the light beam in its focus region has a cross-sectional area which is smaller than 500 $\mu m^2$.

13. The sensor system according to claim 12, wherein the focus region has a cross-sectional area which is smaller than 100 $\mu m^2$ or 24 $\mu m^2$.

14. The sensor system according to claim 13, wherein the cross-sectional area of the light beam expands from its focus region to the intensity sensor by not more than 50%.

15. The sensor system according to claim 1, wherein a collimator and/or an aperture is arranged in the beam course of the light beam behind the light source and in front of the entry into the measurement cell and/or after the measurement cell and in front of the intensity sensor.

16. The sensor system according to claim 1, wherein the light source is formed from a plurality of monochromatic individual light sources, each of the individual light sources having a different wavelength.

17. The sensor system according to claim 1, wherein the intensity sensor is formed from a plurality of individual intensity sensors and comprises a beam splitter which breaks down the light beam which exits from the measurement cell, into a plurality of beams each having a different wavelength which are led to a respective one of the individual intensity sensors.

18. The sensor system according to claim 1, wherein the light beam is led from the light source to the measurement cell through a fibre-optic.

* * * * *